(12) United States Patent
Tsien et al.

(10) Patent No.: US 6,180,411 B1
(45) Date of Patent: Jan. 30, 2001

(54) LIGHT-TRIGGERED INDICATORS THAT MEMORIZE ANALYTE CONCENTRATIONS

(75) Inventors: Roger Y. Tsien, La Jolla; Stephen R. Adams, Poway, both of CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/134,668

(22) Filed: Jul. 30, 1998

Related U.S. Application Data
(60) Provisional application No. 60/054,441, filed on Aug. 1, 1997.

(51) Int. Cl.[7] .................... G01N 33/532; G01N 33/554; C07D 307/82; C07D 491/048
(52) U.S. Cl. ..................... 436/79; 435/7.21; 435/40.5; 436/519; 436/537; 436/805; 548/242; 548/525; 549/60; 549/467; 549/468; 540/461; 546/89
(58) Field of Search .................. 436/79, 537, 519, 436/805; 435/7.21, 40.5; 548/236, 242, 525; 549/468, 467, 60; 540/461; 546/89

(56) References Cited

U.S. PATENT DOCUMENTS

| | | |
|---|---|---|
| 3,817,837 | 6/1974 | Rubenstein et al. . |
| 3,850,752 | 11/1974 | Schuurs et al. . |
| 3,939,350 | 2/1976 | Kronick et al. . |
| 3,996,345 | 12/1976 | Ullman et al. . |
| 4,275,149 | 6/1981 | Litman et al. . |
| 4,277,437 | 7/1981 | Maggio . |
| 4,366,241 | 12/1982 | Tom et al. . |
| 4,603,209 | 7/1986 | Tsien et al. . |
| 4,689,432 | 8/1987 | Tsien et al. . |
| 4,806,604 | 2/1989 | Tsien et al. . |
| 5,141,627 | 8/1992 | Tsien et al. . |
| 5,262,330 | * 11/1993 | Chapoteau et al. ............. 436/79 |
| 5,310,888 | * 5/1994 | Bloczynski et al. ............. 534/767 |
| 5,409,835 | * 4/1995 | Lakowicz et al. ............. 436/79 |
| 5,552,555 | 9/1996 | Tsien et al. . |

FOREIGN PATENT DOCUMENTS 177202   4/1986   (EP) .

OTHER PUBLICATIONS

PNAS USA, Dutton (1979) 76:3392–3396.
Biophysics J., 53:635–39, Kao, Tsien 1988.
J. Biol. Chem., Rogers 1983, 258:5994–97.
J. Biol Chem., Minta 1989, 264:19449–57.
Am. J. Physiol., Raju 1989, 256:C540–48.

* cited by examiner

*Primary Examiner*—Mary E. Ceperley
(74) *Attorney, Agent, or Firm*—Gray Cary Ware & Freidenrich LLP; Lisa A. Haile

(57) ABSTRACT

A new class of optical indicators which are capable of memorizing and preserving the spatial localization of intracellular analytes in a time resolved manner is described. The compounds comprise a chromophore carrying a photolabile group capable of undergoing an irreversible and detectable chemical transformation upon irradiation by light. The chromophore is linked to a binding site capable of binding an analyte, wherein binding of the analyte to the binding site alters an optical property of the chromophore, thus altering the ability of the photolabile group to undergo the chemical transformation. Methods and kits for memorizing the spatial localization of the analytes are also described.

14 Claims, 8 Drawing Sheets

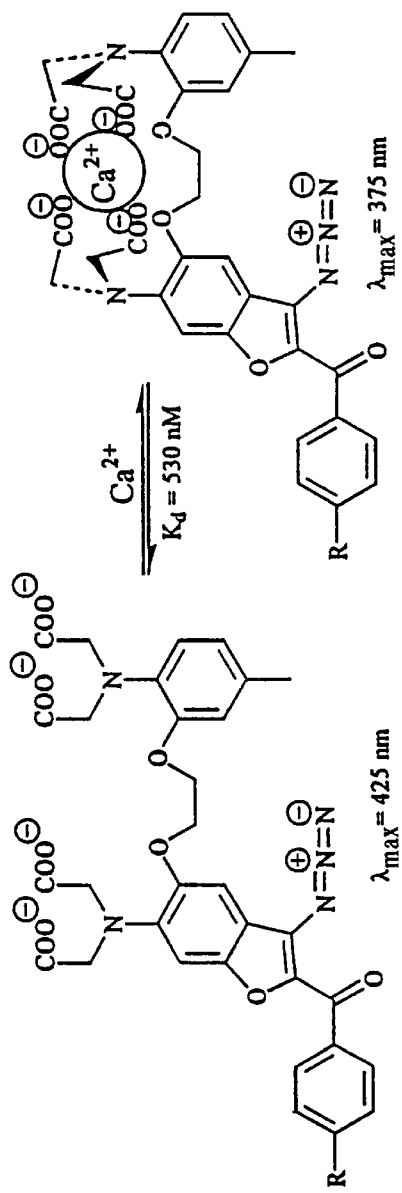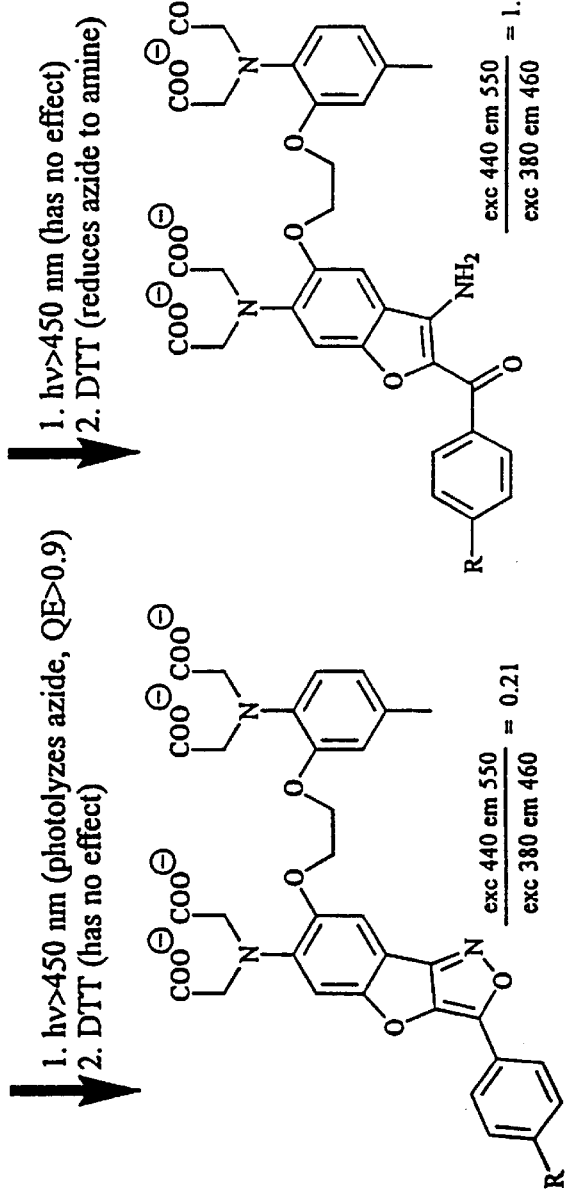
FIG. 3

Memory Dyes

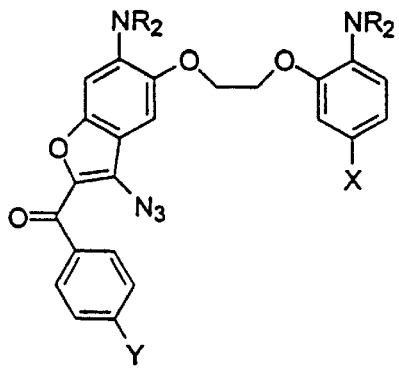

R=CH$_2$CO$_2^-$

Mem-1A  X=CH$_3$  Y=H
Mem-1B  X=CH$_3$  Y=CO$_2^-$
Mem-1C  X=CH$_3$  Y=NH$_2$
Mem-1D  X=CH$_3$  Y= NHAc

Mem-2A  X=CH$_3$. Y=NCS
Mem-2B  X=CH$_3$  Y=CH$_2$CH$_2$NHCO(CH$_2$)$_3$CO$_2$N(COCH$_2$)$_2$

Mem-3A  X=NCS  Y=CO$_2^-$
Mem-3B  X=NHCO(CH$_2$)$_3$CO$_2$N(COCH$_2$)$_2$  Y=CO$_2^-$

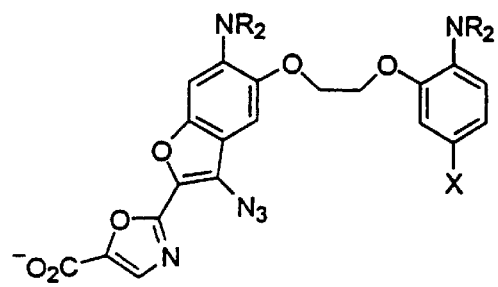

R=CH$_2$CO$_2^-$

Mem-4A  X=CH$_3$
Mem-4B  X=NCS
Mem-4C  X=NHCO(CH$_2$)$_3$CO$_2$N(COCH$_2$)$_2$

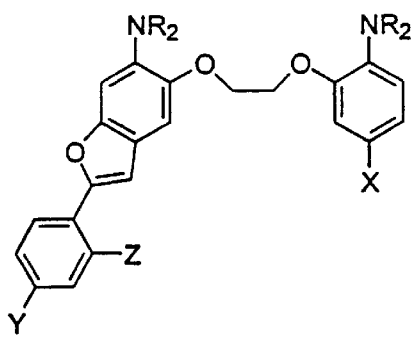

R=CH$_2$CO$_2^-$

Mem-5A  X=CH$_3$  Y=N$_3$  Z=H
Mem-5B  X=CH$_3$  Y=H  Z=N$_3$

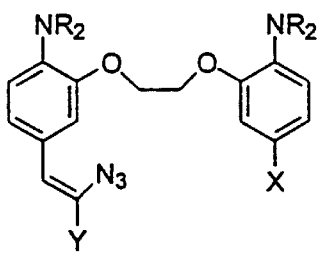

R=CH$_2$CO$_2^-$

Mem-6A  X=CH$_3$  Y=CO$_2^-$
Mem-6B  X=CH$_3$  Y=CONH(CH$_2$)$_2$NH$_2$

FIG. 7

General Synthesis of Memory Dyes: a, phenacyl bromide, $K_2CO_3$, DMF; b, $NOHSO_4$, $HOAc-H_2SO_4$; c, $NaN_3$, $H_2O$; d, KOH, MeOH-dioxane

LIGHT-TRIGGERED INDICATORS THAT MEMORIZE ANALYTE CONCENTRATIONS

CLAIM OF PRIORITY

This application claims priority under 35 U.S.C. §119(e) to U.S. Provisional Patent Application Ser. No. 60/054,441 filed Aug. 1, 1997.

TECHNICAL FIELD

The present invention relates generally to methods of determining analyte concentrations, and more particularly, to photolabile chelators.

BACKGROUND OF THE INVENTION

Although $Ca^{2+}$ is a well established intracellular messenger, there are still many unanswered questions concerning the kinetics and spatial localization of its effects. Because of the importance of calcium as an intracellular messenger, a variety of methods have been developed for measuring intracellular $Ca^{2+}$ levels. The most successful of these use dye-linked chelators which change absorbance or fluorescence upon binding $Ca^{2+}$ ions. Existing indicators for physiological cations such as $Ca^{2+}$, as well as, $Mg^{2+}$, $H^+$, and $Na^+$ change their optical properties reversibly in response to changes in cation concentrations. See, for example, U.S. Pat. No. 4,603,209, and EP 314,480. Chelating compounds have been developed that facilitate changing the intracellular calcium concentration. See, for example, U.S. Pat. Nos. 4,689,432, 4,806,604, and 5,141,627; and EP 177,202, in which a photochemical reaction causes the release or uptake of $Ca^{2+}$ and thereby alters the ambient $Ca^{2+}$.

SUMMARY OF THE INVENTION

In general, the invention features optical indicators which memorize the spatial location and/or concentration of an analyte at a particular chosen point in time. This can allow for time-resolved analysis of analyte concentration. Analysis of the temporal and spatial resolution of the intracellular concentrations of physiologically significant analytes, such as calcium and other cations, can be facilitated by freezing a snapshot of the analyte concentration in the intracellular matrix. The snapshot can allow one to postpone the analysis of the analyte concentration at that particular moment to a later time.

In one aspect, the invention features a compound including a chromophore carrying a photolabile group capable of undergoing an irreversible and detectable chemical transformation upon irradiation by light, the chromophore being linked to or including a binding or chelating site for an analyte. Binding of the analyte to the binding site alters an optical property of the chromophore, thus altering the ability of the photolabile group to undergo the chemical transformation upon irradiation of the compound.

The analyte can be a cation, such as calcium and the chelator can be a BAPTA or BAPTA-like derivative. The chromophore can be any chemical grouping, such as an aromatic, heteroaromatic, or polyene group which absorbs light. One type of photolabile group that photolyzes with high efficiency to an isoxazole is a β-azido, α,β-unsaturated carbonyl group.

In another aspect, the invention relates to a method of memorizing an intracellular concentration of an analyte. The method includes the steps of: (a) loading a cell with an effective amount of a compound as described above under conditions which do not alter the chromophore; (b) irradiating the cell with a wavelength of light which selectively photolyzes the compound to yield a photolyzed product; (c) detecting the presence of the photolyzed product and/or unphotolyzed compound; and (d) relating the presence of the photolyzed product and/or unphotolyzed compound to the intracellular concentration of the analyte. The cell is briefly irradiated. The compound can be bound to the analyte when photolyzed to form the product. Only one form of the compound (i.e., bound or not bound) forms the photolyzed product.

In another aspect, the invention features kits for practicing the above method.

The term "hydrocarbyl" refers to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. Hydrocarbyl can refer to straight chain, branched-chain, cyclic structures or combinations thereof.

The term "alkyl" refers to a branched or straight chain acyclic, monovalent saturated hydrocarbon radical of one to twenty carbon atoms.

The term "lower-alkyl" refers to an alkyl radical of one to six carbon atoms. This term is further exemplified by such radicals as methyl, ethyl, n-propyl, isopropyl, isobutyl, sec-butyl, n-butyl and tert-butyl, n-hexyl and 3-methylpentyl.

The term "alkenyl" refers to an unsaturated hydrocarbon radical which contains at least one carbon—carbon double bond and includes straight chain, branched chain and cyclic radicals.

The term "alkynyl" refers to an unsaturated hydrocarbon radical which contains at least one carbon-carbon triple bond and includes straight chain, branched chain and cyclic radicals.

The term "acyl" refers to the group R—C(O)—, wherein R represents a hydrocarbyl group or a heterocyclic or homocyclic aromatic group.

The term "lower" referred to herein in connection with organic radicals or compounds respectively defines such with up to and including six, preferably up to and including four carbon atoms. Such groups may be straight chain or branched.

The term "aryl" refers to an aromatic carbocyclic radical having a single ring (e.g., phenyl) or multiple condensed rings (e.g., naphthyl, anthracenyl). Aryl radicals can be optionally substituted with substituents exemplified, but not limited, to those listed below.

The term "heterocyclic aromatic" refers to an aromatic mono- or poly-cyclic radical having at least one heteroatom within a ring, e.g., nitrogen, oxygen, or sulfur. For example, typical heteroaryl groups with one or more nitrogen atoms are tetrazoyl, pyrrolyl, pyridyl (e.g., 4-pyridyl, 3-pyridyl, 2-pyridyl), pyridazinyl, indolyl, quinolyl (e.g., 2-quinolyl, 3-quinolyl, etc.), imidazolyl, isoquinolyl, pyrazolyl, pyrazinyl, pyrimidinyl, pyridonyl or pyridazinonyl; typical oxygen heteroaryl radicals with an oxygen atom are 2-furyl, 3-furyl or benzofuranyl; typical sulfur heteroaryl radicals are thienyl, and benzothienyl; typical mixed heteroatom heteroaryl radicals are furazanyl, oxazolyl, isoxazolyl, thiazolyl, and phenothiazinyl. Further the term also includes instances where a heteroatom within the ring has been oxidized, such as, for example, to form an N-oxide or sulfone. Heterocyclic aromatic radicals can be optionally substituted with substituents exemplified, but not limited, to those listed below.

The term "optionally substituted" refers to the presence or lack thereof of a substituent on the group being defined. When substitution is present, the group may be mono-, di- or tri-substituted, independently, with alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, and di-lower-alkylcarbamoyl. The substituent can be a carboxylic acid, ester, sulfonamides, phosphono or phosphoryl group, or arsono group.

The term "pharmaceutically acceptable salt" refers to those salts which retain the biological effectiveness and properties of the free bases or free acids and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, benzoic acid, fumaric acid, tartaric acid, citric acid, benzoic acid, cinnamic acid, mandelic acid, methanesulfonic acid, ethanesulfonic acid, p-toluene-sulfonic acid, salicylic acid and the like; or inorganic or organic bases.

The term "pharmaceutically acceptable ester" refers to those nontoxic readily hydrolyzable esters conventionally used in the pharmaceutical industry, especially α-acyloxyalkyl esters, such as acetoxymethyl esters. The invention contemplates those compounds of which are esters as described herein and at the same time are the pharmaceutically acceptable acid addition salts thereof. It is contemplated that pharmaceutically unacceptable salts and esters could be used if pharmaceutical acceptability were not desired, such as in certain in vitro studies.

The term "effective amount" refers to the amount which is necessary to create a desired effect. In the case when the desired effect is to determine accurately the intracellular concentration of an analyte by its binding to a photolyzable compound of this invention, the effective amount of the photolyzable compound (or its precursor) is that amount which allows that determination.

The term "$[Ca^{2+}]_i$" refers to the intracellular calcium ion concentration.

The term "chromophore" refers to a chemical grouping which when present in a compound (the chromogen) results in the displacement of, or appearance of, absorbent bands in the optical spectrum of the compound. Typically, the presence of the chromophore gives color to the compound by causing shifts in the visible or ultra-violet spectrum.

The term "fluorophore" refers to a chemical grouping which when present in a compound (the fluorogen) which is irradiated with light results in the compound emitting light of a wavelength different to the irradiated light. Typically, the wavelength of the emitted light is of longer wavelength than that of the irradiating light.

The term "photolyzable" or "photolabile" refers to a compound or chemical grouping, which when irradiated with light of an appropriate wavelength, undergoes a chemical transformation. Such chemical transformations can involve the making and/or breaking of covalent bonds in the compound.

The term "quantum efficiency" refers to the yield of product in a photochemical reaction compared to the amount of light applied.

As used herein, MOPS means 3-N-morpholino)-propanesulfonic acid.

As used herein, EGTA means ethylene glycol bis(-beta-aminoethyl ether)-N,N,N',N'-tetracetic acid.

As used herein, BAPTA means 1,2-bis(2-aminophenoxy)-ethane-N,N,N'N'-tetraacetic acid.

As used herein, BAPTA-like means substituted derivatives of BAPTA which retain the essential characteristic of two bis(carboxymethyl)amino-substituted phenyl rings, the rings being linked at the positions ortho to the amines through a four atom bridge wherein the atom adjacent to each phenyl ring is N or O and the two center atoms are each C. By this definition, it is meant that "BAPTA-like" can include compounds like quin-1 and quin-2.

As used herein, quin-1 means 2-[[2-[bis(carboxymethyl) amino]-5-methylphenoxy]methyl]-8-[bis(carboxymethyl) amino]-quinoline.

As used herein, quin-2 means 2-[[2-[bis(carboxymethyl) amino]-5-methylphenoxy]-methyl]-6-methoxy-8-[bis (carboxymethyl)amino]-quinoline.

As used herein, nitr-7 means cis-1-(2-bis(carboxymethyl) amino-5-(1-hydroxy-1-(2-nitro-4,5-methylenedioxyphenyl) methyl)phenoxy)-2-(2-bis(carboxymethyl)amino-5-methylphenoxy)cyclopentane.

BAPTA and BAPTA-like compounds that can be used as starting materials can be obtained, for example, from Molecular Probes, Eugene, Oreg.

BRIEF DESCRIPTION OF THE DRAWINGS

FIG. 3 shows the snapshot memorization of intracelular $Ca^{2+}$ using mem-1 by irradiating at >450 nm, reducing unphotolyzed mem-1 to an amine with dithiothreitol (DTT) and differentially detecting the photolyzed product, the isoxazole and the unphotolyzed product, the amine by fluorescence spectroscopy.

FIG. 7 shows structures of aromatic azido-BAPTA linked memory indicators.

DESCRIPTION OF THE PREFERRED EMBODIMENTS

Memory Indicators

Figure 1:
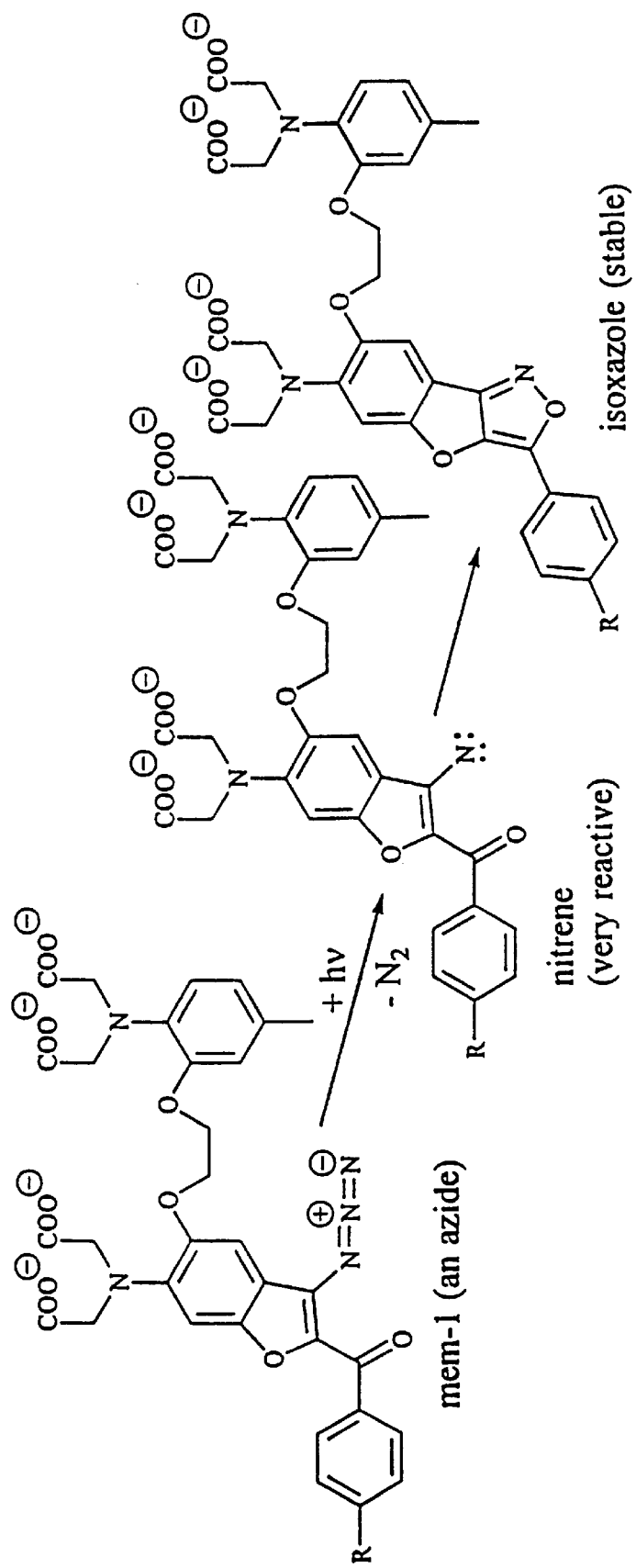
FIG. 1 shows the photochemistry of the mem-1 $Ca^{2+}$ binding compound.

The invention features molecules that can be triggered by appropriate wavelengths of light to memorize the instantaneous spatial pattern of an ambient analyte as a stable snapshot that can be read out later, even after the analyte concentration has changed or the biological tissue has been fixed. The advantages of such analyte-memorizing molecules are that analyte concentrations can be simultaneously and instantly recorded in much larger numbers of cells or volumes of tissue and at much higher spatial and temporal resolution than presently possible. This improvement is because the final readout or imaging can be performed at leisure by optical cytometry or electron microscopy, after specimen fixation if desired, rather than in real time by imaging of the living tissue.

The molecules are composed of a binding site which is capable of binding or coordinating an analyte, a chromophore, and a photolabile group. The photolabile group undergoes an irreversible and detectable chemical transformation when the chromophore absorbs light. The binding site and the chromophore are linked in such a manner that the absorbance spectrum of the chromophore shifts when analyte binds to the binding site. Therefore, analyte binding renders the photolabile group more or less likely to undergo the photochemical transformation by a defined wavelength of light. For example, if analyte binding shifts the absorbance spectrum to shorter wavelengths, photolysis at a longer, defined wavelength converts molecules which are unbound by analyte to a different species, whereas molecules which were bound by analyte remain unchanged. Either or both of the original compound and reaction product from the photolysis can be detected subsequently. Since the reaction ceases when irradiation is stopped, the formation of the photolysis reaction product provides an imprint which freezes into place the analyte concentration which existed at the moment of irradiation, in both a spatial and temporal sense, preserving it for subsequent detection.

These compounds include a chromophore incorporating a photolabile group capable of undergoing an irreversible and detectable chemical transformation upon irradiation by light, the chromophore being linked to a binding site capable of binding an analyte, wherein binding of the analyte to the site alters an optical property of the chromophore, thus altering the ability of the photolabile group to undergo the chemical transformation upon irradiation at a defined wavelength of light. Such compounds can be represented by the generic formula I:

$$P\text{-}C\text{-}B \qquad \qquad \text{I}$$

where P represents a photolabile group, C represents a chromophore and B represents a binding site which is capable of binding an analyte.

Photolabile groups are those groups which undergo an irreversible chemical transformation when irradiated with light. In this context, an "irreversible chemical transformation" refers to any transformation which results in the making or breaking of one or more covalent bonds. Thus, groups which do no more than undergo cis-trans isomerization of a carbon-carbon double bond are not categorized as photolabile groups in the context of this invention. Representative, but non-limiting examples of photolabile groups can be found in "Photolytic Deprotection and Activation of Functional Groups", by V. N. Pillai in *Organic Photochemistry*, A. Padwa (eds.), 9:225–323 (1987) (Marcel Dekker). Preferred photolabile groups for use in biological systems are those which undergo photolysis at wavelengths above 300 nm, preferably above 350 nm, since at these wavelengths most proteins, nucleic acids and other cellular constituents will not strongly absorb light and thus are less likely to undergo degradative or competitive reactions. The photolabile group can be attached to or partially or wholly embedded into a chromophore.

Azides, particularly aromatic azides, which undergo photolysis with relatively high efficiency are favored photosensitive groups (Reiser, A., Wagner, H. M. (1971) "Photochemistry of the azido group", in *The Chemistry of the Azido Group* (S. Patai, ed.), pp. 441–501. New York: Wiley). An example of a photolabile group disclosed herein is a β-azido, α,β-unsaturated carbonyl group. Upon irradiation with light of a suitable wavelength, the azido group extrudes nitrogen and the resulting nitrene cyclizes to an isoxazole. An azide can insert into a number of other chemical groups such as, but not limited to, nitro (to form a furoxan), azo (to form a triazole), carbon—carbon double bond (to form an indole), carbon-nitrogen double bond (to form a pyrazole or imidazole). Such groups can be incorporated into adjacent heterocyclic (e.g., pyridines or isoxazole) or aryl (e.g. phenyl, substituted phenyl rings). In addition, azides which are not adjacent to a suitable functionality will produce characteristic and defined products through well-known ring expansions (e.g., to form benzazirines) or addition reactions to intermediate reactive species such as nitrenium ions formed from nitrenes in aqueous reactions. Such products are distinctive and can be differentiated from the unphotolyzed precursor. Azides incorporated into carbon-carbon double bonds (e.g. vinyl azides) can also be used as they form distinctive azirine products upon photolysis.

Other photolabile groups which can be utilized include diazoketones that produce carboxylic acids on photolysis. Suitably attached nitrobenzyl groups photolyze to a nitrosobenzaldehyde or nitrosoacetophenone derivatives often with release of a carboxylic acid, alcohol, phosphate, amine, or amide.

As a result of the photolytic transformation, the photolytic reaction product will be different from and thereby distinguishable from the precursor unphotolyzed compound. Most conveniently, this distinction will be made based on some optical property of the compound, e.g., absorbance or fluorescence. However, as described below, the presence of the photolyzed reaction product can also be detected with specific binding reagents such as antibodies.

Typically, the photolabile group undergoes an irreversible reaction when exposed to light of an appropriate wavelength.

The chromophore can be any chemical grouping which absorbs light. Generally, chromophores will have at least one double bond, preferably a series of conjugated double bonds. Typical chromophores include aromatic and heteroaromatic groups, optionally substituted with electron donating or electron withdrawing groups. Many chromophores are known to those of skill in the art and this invention is not intended to be limited to particular groups of chromophores.

The chromophore is attached to an analyte binding site in a manner such that binding of analyte by the binding site alters an optical property of the chromophore thus allowing detection of binding of analyte to the compound. Generally, this is accomplished by a linkage between chromophore and binding site which allows for electronic coupling of the chromophore to the binding site. Typically, this electronic coupling is maintained by π-electron conjugation via carbon-carbon double and triple bonds, aromatic rings and lone pair electrons of heteroatoms. If linked by carbon-carbon bonds, as long as there is no more than one sigma bond in a row between the chromophore and the binding site, this electronic coupling will be maintained. The binding site may be linked to the chromophore via a single point of attachment or multiple points of attachment as is the case with binding sites which are fused onto the chromophore. The link between the chromophore and the binding site of the compound may also be a complex aromatic group or aromatic heterocycle, which in turn can be part of the chromophore or part of the binder or both.

In one embodiment of this invention, compounds disclosed herein have a structure represented by an azido-substituted aromatic ring A with additional substituents Y and Z and are represented by the formula:

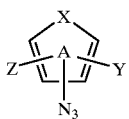

and the pharmaceutically acceptable salts and esters thereof, wherein:

X is independently O, NH, S or CH=CH;

Y is an aromatic or heteroaromatic group carrying the binding site capable of binding an analyte and is fused or attached to a single atom of A;

Z is a substituent attached to A ortho to the azido group and is represented by R—C(O)—, wherein R is independently a hydrocarbyl radical or a heterocyclic aromatic radical. Examples include X=O, and Y=BAPTA where the furan ring is fused to one of the benzene rings of BAPTA. The compounds can be made by one of skill in the art.

Particular compounds are represented by the formula:

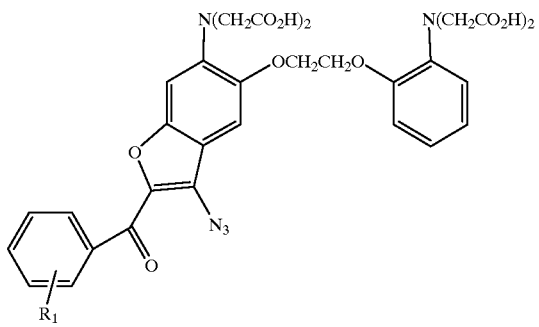

and the pharmaceutically acceptable salts and esters thereof, wherein $R_1$ is independently selected from the group consisting of acyl, carboxy, sulfonamido, phosphono, hydrocarbyl, cyano, and nitro. Structures of suitable compounds are shown in FIG. 7.

Other particular compounds are represented by the formula:

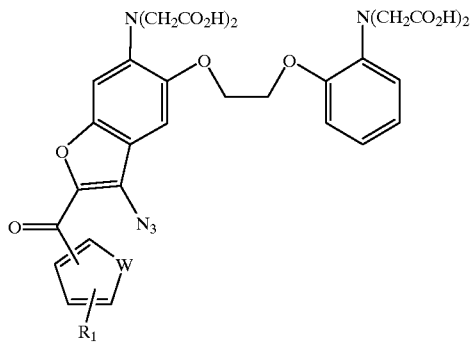

and the pharmaceutically acceptable salts and esters thereof, wherein:

W=O, S, NH, $NR_2$, with $R_2$ being aryl, heterocyclic aromatic, alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, di-lower-alkylcarbamoyl, carboxylic acid, ester, sulfonamide, phosphono, phosphoryl group, or arsono, and wherein $R_1$ is independently selected from the group consisting of acyl, carboxy, sulfonamido, phosphono, hydrocarbyl, cyano, and nitro.

The compounds may be additionally derivatized to facilitate loading into a biological cell. Frequently, the compounds will be membrane-permeant, readily hydrolyzable esters, such as α-acyloxyalkyl esters (e.g., acetoxymethyl) as are known in the pharmaceutical industry.

Binding of the analyte to the binding site alters an optical property of the chromophore such that the photolabile group is selectively protected from undergoing the photolytic chemical transformation. Typically, this is accomplished by a shift in the absorption spectrum of the chromophore when analyte binds to the binding site. For example, if analyte binding shifts the absorbance of the chromophore to a shorter wavelength, irradiation at a longer wavelength will not affect the photolabile group on the chromophore on analyte-bound compounds because they will not absorb the longer wavelength light energy. However, compounds which are not bound to analyte will absorb light energy at the longer wavelength and thus photolytic chemical transformation of the photolabile group will occur. The converse will hold for compounds in which analyte binding shifts the absorbance spectrum of the compound to longer wavelength. Irradiation at shorter wavelengths will result in selective photolysis of compound not bound to analyte. Because many chelating optical indicators shift their absorbance maxima to a substantial extent upon analyte binding, it generally will be possible to attach any of a wide variety of photolabile groups to an existing optical indicator and find a band of wavelengths at which there is a large difference in absorbance between the free and analyte-bound forms of the indicator. Irradiation at a selected wavelength as described above will result in photolysis and transformation of the photolabile group on the unprotected (i.e., analyte-unbound) indicator, thus allowing the detection of analyte-bound compound. One skilled in the art will recognize that one can also detect remaining unphotolyzed compound and derive similar information about analyte concentrations. In certain systems, some of which are exemplified below, it is desirable to detect both the photolyzed product and the unphotolyzed compound.

Alternatively, binding of the analyte can result in an increase (or decrease) in the absorbance intensity of the indicator, thus rendering the indicator more or less likely to photolyze. In compounds of this type, the absorption maxima can remain unchanged, but the intensity of the absorption can be altered. When a change in an optical property (e.g., absorbance or fluorescence) between photolyzed and unphotolyzed product is being used to derive an instantaneous snapshot of an analyte concentration, the change is ideally large enough to allow for good discrinmination between them. The shift in absorbance maxima or fluorescence excitation or emission maxima is typically at least about 25 nm, preferably about 50 nm and more preferably about 100 nm. If the shift in wavelength is not sufficiently large and a high degree of spectral overlap exists between the compounds, one can still achieve good discrimination by irradiating/detecting with selected band pass/cut off filters or using a laser to irradiate at a specific wavelength.

The binding sites that are present in the compounds of this invention are determined by the analyte that is being detected. In many cases the binding site will be a multidentate ligand which is capable of chelating the analyte. Crown ethers and cryptands can be used when the analyte being detected is a cation. The precise structural requirements which provide selectivity for one cation over another are known to those of skill in the art and will not be elaborated here. A particularly useful class of ligands is based on a octacoordinate tetracarboxylate chelating unit, such as, for example, is contained in an ethylene glycol bis(-beta-aminoethyl ether)-N,N,N',N'-tetracetic acid unit (EGTA). BAPTA and BAPTA-like derivatives can also be used as chelating units in memory indicators.

Methods of Memorizing Analyte Concentrations

The compounds described above can be used to "memorize" the intracellular concentration of an analyte. Biologically significant analytes include cations such as $Ca^{2+}$, as well as, $Mg^{2+}$, $H^+$, and $Na^+$. The methods include the steps of: (a) loading a cell with an effective amount of a memory indicator described earlier under conditions which do not alter the chromophore; (b) irradiating the cell with a wavelength of light which selectively photolyzes indicator which is not bound to the analyte, to form a chemically transformed product; (c) detecting the presence of the transformed product and/or unphotolyzed indicator; and (d) relating the presence of the transformed product and/or unphotolyzed indicator to the intracellular concentration of the analyte.

Most of the memory indicators disclosed by this invention are light sensitive, particularly to visible light and will photodegrade under ambient light conditions. Therefore, they typically can be loaded into the cell in the dark and then exposed to light of the appropriate wavelength. When carboxylic acid groups are present in the memory indicators, the compounds can be used as their α-acyloxyalkylester derivatives (e.g., acetoxymethylesters). Alternatively, the compounds can be loaded by direct microinjection, scrape loading, patch clamp techniques and the like.

It will frequently be necessary to destroy unphotolyzed indicator prior to detecting the presence and location of the photolyzed product. This is particularly true when the method of detection involves another irradiation step, albeit at a different wavelength, such as when one uses absorbance or fluorescence. Any convenient method can be used to destroy unphotolyzed indicator and the method will usually be determined by the functionality present in the photolabile group. For example, when the photolabile group is an azide, a convenient biologically compatible method which will not destroy the cellular integrity of the sample is reduction, e.g. with a thiol or dithiol such as for example, but not limited to, dithiothreitol (DTT), dithioerythritol (DTT), or a mild inorganic reductant (e.g., a hydride reductant such as for example, sodium cyanoborohydride).

The photolyzed and/or unphotolyzed indicators can be conveniently detected by fluorescence ratio imaging techniques as described in more detail below. Alternatively, the indicators can be detecting by staining with labelled specific binding reagents, such as monoclonal or polyclonal antibodies. The reagents can be used as labelled derivatives and their binding detected directly or any of a variety of labelled secondary reagents can be used to detect the presence of the first binding reagent.

Antibodies that can be used include any immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof, which immunoglobulins include the various classes and isotypes, such as IgA (IgA1 and IgA2), IgD, IgE, IgM, and IgG (IgG1, IgG2, IgG3, and IgG4) etc. Fragments thereof may include Fab, Fv and F(ab')$_2$, Fab', and the like.

Useful labels that can be used to detect binding of a primary or secondary reagent in the present invention include biotin for staining with labeled streptavidin conjugate, magnetic beads (e.g., Dynabeads™), fluorescent dyes (e.g., fluorescein, Texas Red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others along with their precipitating substrates commonly used in histochemical staining), colorimetric labels such as colloidal gold or colored glass or plastic (e.g., polystyrene, polypropylene, latex, etc.) beads and chemiluminescent labels. Patents teaching the use of such labels include U.S. Pat. Nos. 3,817,837; 3,850,752; 3,939,350; 3,996,345; 4,277,437; 4,275,149; and 4,366,241.

Another aspect of the invention provides a kit including a compound capable of memorizing the concentration of an analyte as described above, detection reagents and instructions for their use.

The Mem-1 Indicator

Figure 2:
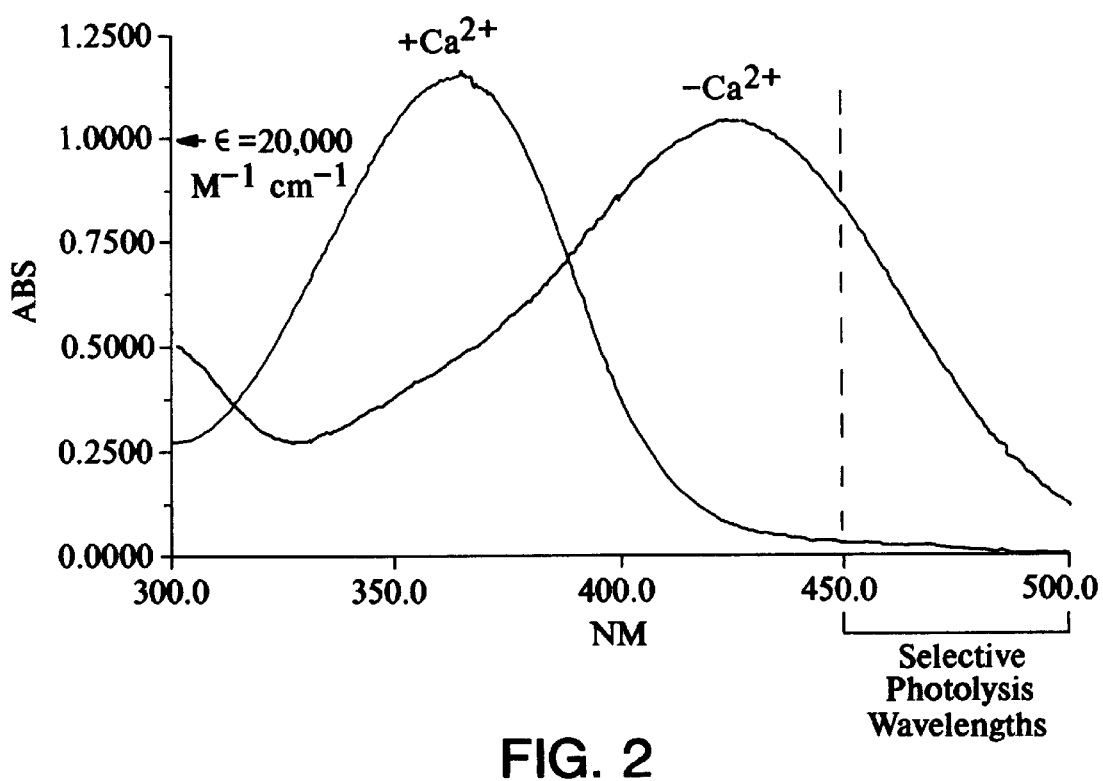
FIG. 2 shows the absorbance spectra of mem-1 bound or unbound to $Ca^{2+}$.

A suitable class of molecules whose photochemistry is controlled by $Ca^{2+}$ is shown in FIG. 1 as "mem-1". When the molecules are $Ca^{2+}$-free, they absorb light at >420 nm and undergo a ready photochemical reaction whose probable course is shown in FIG. 1. This reaction proceeds by extrusion of $N_2$ from the azide group to give a nitrene, which attacks the adjacent carbonyl group to give an isoxazole ring. Mem-1 when $Ca^{2+}$-free has an absorbance peak at 425 nm ($\epsilon$=20,000 $M^{-1}cm^{-1}$), which shifts to 375 nm ($\epsilon$=23,000 $M^{-1}cm^{-1}$) when $Ca^{2+}$ binds (FIG. 2). For wavelengths >420 nm, the $Ca^{2+}$-free form absorbs much more strongly than the $Ca^{2+}$ complex, so that the former photolyzes about 20-fold faster than the latter. Thus, near 420–440 nm, the sensitivity to light or product of the photolysis quantum efficiency and extinction coefficient is 2700 $M^{-1}cm^{-1}$ for the free dye compared to 134 $M^{-1}cm^{-1}$ for its $Ca^{2+}$ complex. High $[Ca^{2+}]_i$ can protect mem-1 from visible-light photolysis by shifting the absorbance peak into the ultraviolet. Because many optical indicators shift their absorbance maxima to a substantial extent upon cation binding, and because azides attached to chromophores generally photolyze with high efficiency, it should be possible in most cases to attach an azide moiety to such an existing cation indicator and find a band of wavelengths at which there is a large difference in absorbance and photolytic sensitivity between the free and cation-bound forms of the indicator. In the case of mem-1, the $Ca^{2+}$ dissociation constant is about 530 nM, so that in resting unstimulated cells where $[Ca^{2+}]_i$ is <100 nM, mem-1 will be largely $Ca^{2+}$-free and photolyzable at wavelengths >420 nb, whereas in activated cells or regions of cells where $[Ca^{2+}]_i$>1 μM, the mem-1 will be resistant to such wavelengths. Restriction to wavelengths >450 nm will give the highest discriminations between the free and $Ca^{2+}$-bound forms at the cost of requiring somewhat higher light intensities.

If subcellular resolution is desired, attachment to cell macromolecules is necessary to prevent difflusion of the probe after flashing and during fixation. Mem-1 has been prepared with R=NCS (isothiocyanate) and other amine-reactive groups such as N-hydroxysuccinimide esters. Other functionalities which can be used to label macromolecules can be found in the *Handbook of Protein Conjugation (CRC Press,* 1991). It has been verified that such molecules label amino acids or proteins such as serum albumin within a few minutes, and that the conjugates retain the relevant properties desired (the above spectral and binding data were obtained on the glycine conjugate, (R=NHCSNHCH$_2$COO$^-$). The isothiocyanate also seems to attach to proteins in real cells, because within a few minutes after injection into cells such as fibroblasts, some dye was retained upon cell permeabilization.

Mem-1 would be used by ester-loading or injection or perfusion into cells, then waiting briefly for covalent attachment, all the while avoiding illumination <500 nm. In other words, it would be handled only in the dark or under yellow or red safelight illumination. At the appropriate moment for [Ca$^{2+}$]$_i$ to be recorded, at a desired interval after physiological or pharmacological stimulation of the tissue, a flashlamp with appropriate wavelength filters or a laser would be fired to illuminate the tissue at wavelengths of 450–500 nm. Spatially uniform illumination will trigger a photochemical change in predominantly those molecules sitting in regions of low [Ca$^{2+}$]$_i$, whereas where [Ca$^{2+}$]$_i$ is high, the molecules will be mostly unaffected because they had bound Ca$^{2+}$ and could not absorb the triggering photons. Finally, the tissue will be frozen and/or fixed by conventional means and prepared for cytometry, fluorescence microscopy, or immunohistochemistry to map the extent of photolysis.

Direct fluorescence cytometry or microscopy would rely on the fluorescence of the isoxazole photolysis product of mem-1, whose excitation maximum is 354–385 nm depending on Ca$^{2+}$, and emission maximum is 490 nm. In order to monitor this fluorescence without photolyzing previously unphotolyzed mem-1, the azide groups are removed by reduction to amino groups, for example using a dithiol such as dithiothreitol or 1,3-propanedithiol (Bayley, H., Standring, D. N., Knowles, J. R. (1978) *Tetrahedron Lett.* 36, 33–3634). This step does not affect the isoxazole, and is analogous to the need to put photographic film in fixer to remove unreacted silver halide before turning on the room lights. The chemical reduction of the azide takes a few minutes at room temperature and produces an amine that is fairly photostable and also fluorescent. Its excitation and emission are at longer wavelengths than those of the isoxazole photoproduct, so fluorescence ratio imaging can distinguish isoxazole photoproduct from unphotolyzed mem-1 reduced to amine.

Figure 4:
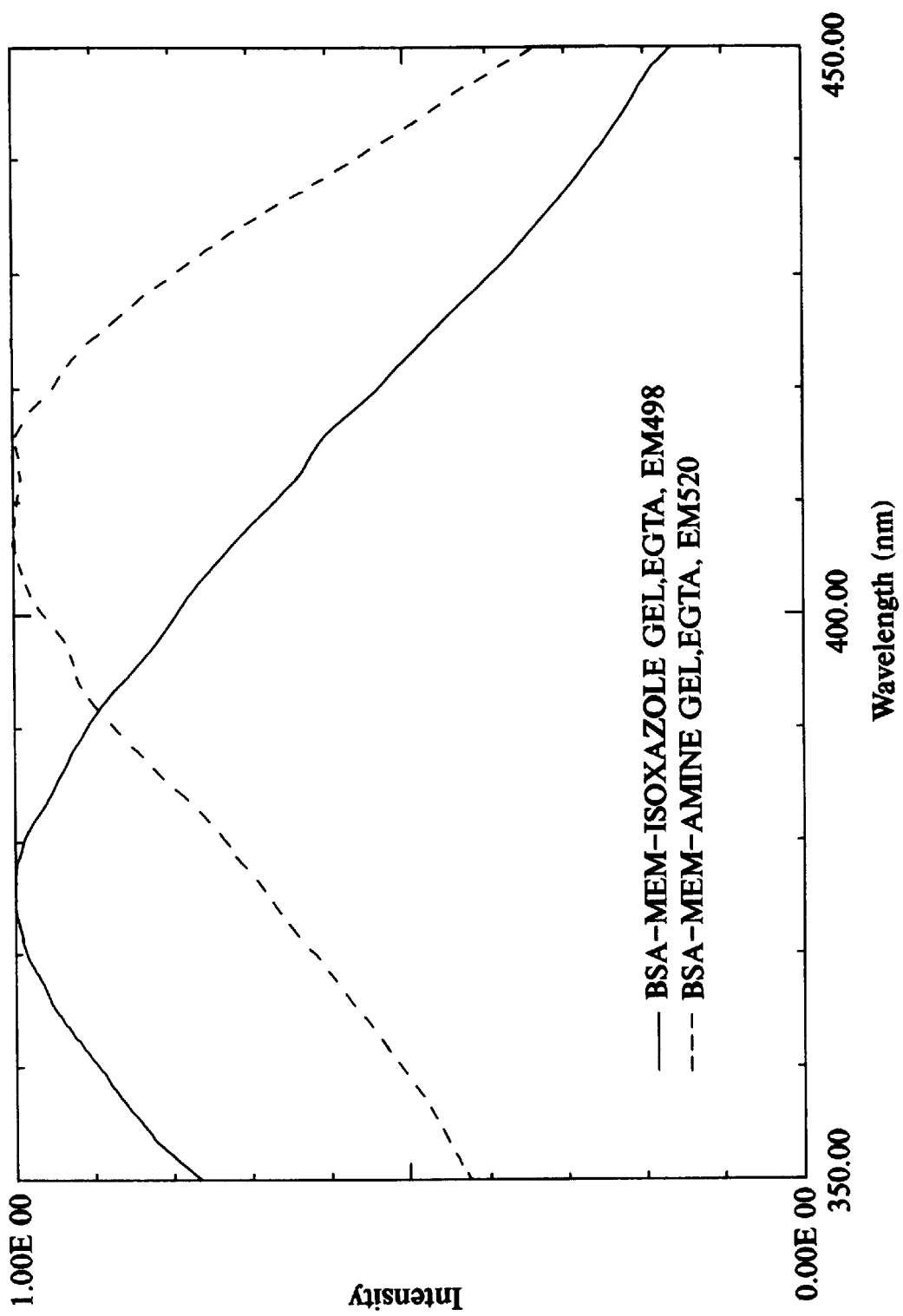
FIG. 4 shows fluorescence excitation spectra of the photolysis product, the isoxazole, and unphotolyzed product, the amine.
Figure 5:
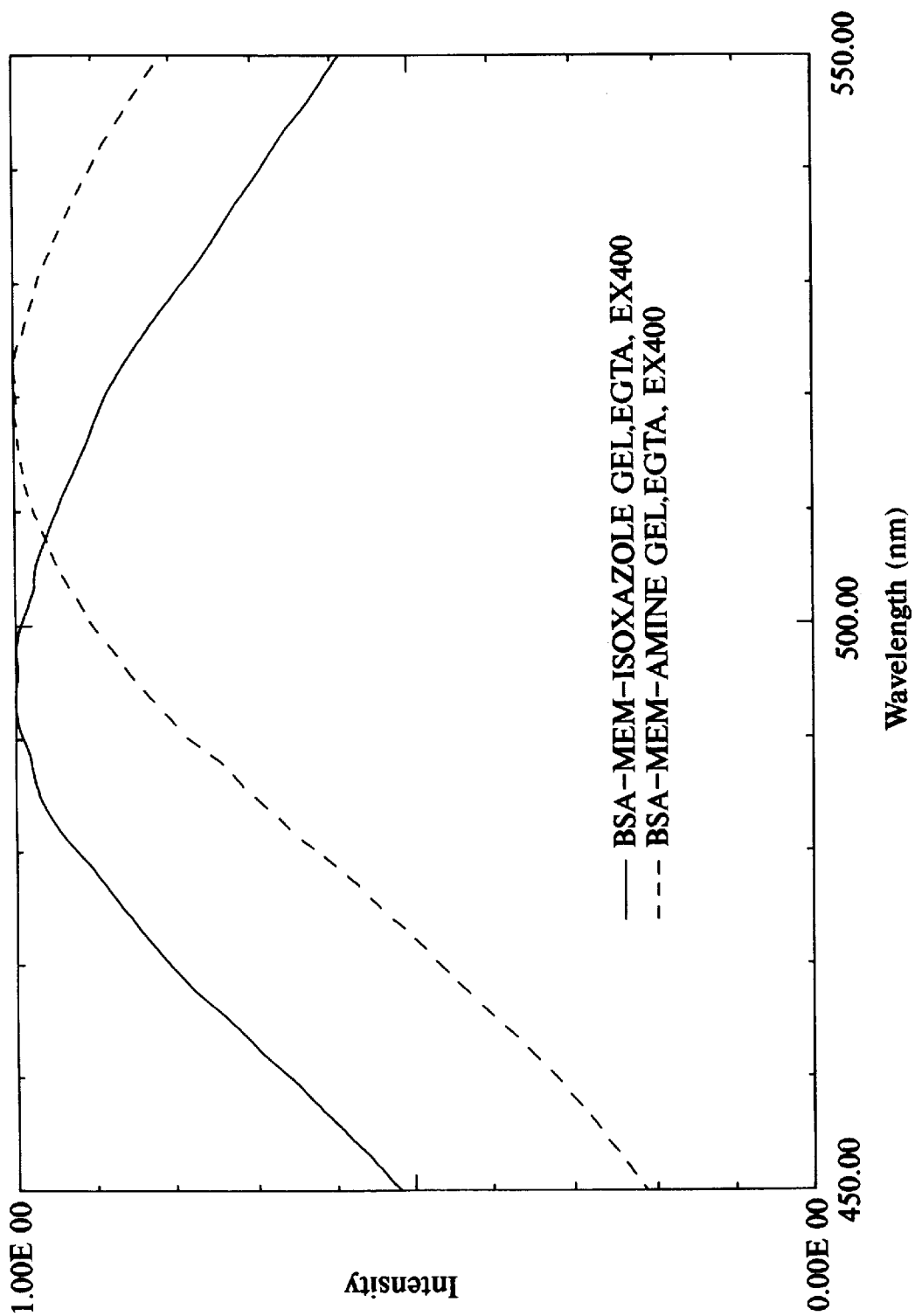
FIG. 5 shows fluorescence emission spectra of the photolysis product, the isoxazole, and unphotolyzed product, the amine.

FIG. 3 summarizes the chemistry of photolysis vs. reduction: mem-1 in low Ca$^{2+}$ takes the left-hand path to the isoxazole, whereas in high Ca$^{2+}$ it takes the right-hand path to the amine. FIG. 4 compares the normalized excitation spectra of the isoxazole photoproduct (solid line, peaking at 376 nm) and the amine reduction product (dashed line, peaking at 408 nm), each separately coupled to bovine serum albumin (R=NHCSNH . . . protein), fixed with dimethyl suberimidate, and measured in Ca$^{2+}$-free conditions (excess EGTA). FIG. 5 shows the corresponding emission spectra, peaking at 498 nm (isoxazole) and 520 nm (amine) respectively. The excitation and emission wavelengths that maximize the distinguishability of the isoxazole from the amine are not the above peaks but are displaced to either side, namely 380 nm excitation, 460 nm emission vs. 440 nm excitation, 550 nm emission. The ratio of fluorescences at these two wavelength sets changes from 0.21 for pure isoxazole to 1.74 for the pure amine. Intermediate [Ca$^{2+}$]$_i$ concentrations giving rise to mixtures of isoxazole and amine would give intermediate fluorescence ratios that could be calibrated back to the [Ca$^{2+}$]$_i$ values.

An alternative method for detecting the extent of photolysis would be to expose the tissue sections to specific antibodies (polyclonals or monoclonals) previously raised against protein conjugates of the photolyzed or unphotolyzed indicator. Both are the right size to be haptens, are separately available as pure chemical species, and are already conveniently flurnished with reactive groups for conjugate to carrier proteins or to affinity columns for antibody purification by adsorption of cross-reacting species. Antibodies are known to make structural discriminations much subtler than the differences between the isoxazole photoproduct and the starting azide or the amine reduction product (Pressman, D., Grossberg, A. L. (1968) *The Structural Basis of Antibody Specificity*. (New York: Benjamin); Karush, F. (1962) *Adv. Immunol.* 2:1–40), so raising discriminating antibodies should be possible. If necessary, monoclonal antibodies would be generated. The antibodies can be labelled with any of a variety of conventional labels and thereby visualized. For example, the antibodies would then be labelled and visualized by conventional fluorescein or rhodamine, that are excited or that emit at wavelengths different from the mem-1 products. Alternatively fluorescently-labeled antibodies against the first antibodies would be applied as in conventional indirect "sandwich" immunofluorescence. If visualization by electron microscopy is needed, this would simply require substitution of electron-dense labels such as ferritin, colloidal gold, iron-dextran complexes, or peroxidase-antiperoxidase complexes (Stemberger, L. A. (1986) *Immunocytochemisty,* 3rd ed. New York: Wiley). Ideally one would stain simultaneously and independently for both the photolyzed and unphotolyzed indicator species, for example with a fluorescein-labeled antibody to the photolyzed and rhodamine-labeled antibody to the unphotolyzed. The ratio of red to green immunofluorescence would then reflect the [Ca$^{2+}$]$_i$ during the flash. If one stained for only one species, say the photolyzed, an absence of stain could mean either that [Ca$^{2+}$]$_i$ had been very high or that insufficient indicator had penetrated into that region of cytoplasm. Ratio recording removes that ambiguity. Ratio recording in electron microscopy is possible with a pair of distinguishable labels such as ferritin and iron dextran (Dutton, A. H., Tokuyasu, K. T., Singer, S. J. (1979) *Proc. Natl. Acad. Sci.* U.S.A. 76:3392–3396) or large and small gold particles (DeMey, J. (1983) "Colloidal gold particles in immunocytochemistry", in *Immunocytochemistry: Practical Applications in Pathology and Biology* (J. M. Polak and S. Van Noorden, eds). Bristol: Wright PSG), or one could apply alternate antibodies to alternate serial sections.

Regardless of the approach used to measure photolysis, this method will sacrifice continuous recording in favor of spatial resolution during a single photochemical exposure. All other methods at present make the opposite choice. Spatial resolution would be particularly valuable in neurobiological applications, since adjacent neurons are generally expected to be doing different things while processing information. It would also be highly valuable in pharmaceutical screening of large numbers of compounds in parallel, for example arising from combinatorial libraries, because the peak response of cells to each compound could be resolved. The limit on time resolution will be set by the rapidity with which the indicator binds and releases Ca$^{2+}$, which for this class of indicator is typically in the millisecond time domain (Kao, J. P. Y., Tsien, R. Y. (1988) *Biophys.*

J 53: 635–639). Photodynamic damage should not be important because it can hardly build up significantly in a millisecond of flash illumination. This method is much more tolerant of mechanical thickness, light scattering and tissue pulsation than any method trying to measure images of live tissue. As long as the photolysis flash can penetrate the tissue, randomization of the photon paths is irrelevant. Mechanical thickness and light scattering are also unimportant during readout because the tissue will have been sectioned and cleared.

The concentration of intracellular dye should not need to exceed a few micromolar, because immunocytochemistry is known to be able to trace proteins whose concentration in cytoplasm is not greater. Such low concentrations have usually been easily attained or exceeded by intracellular hydrolysis of membrane- permeant esters. Micromolar concentrations of cytoplasmic $Ca^{2+}$ chelators have generally been without effect on physiological responses because higher concentrations of $Ca^{2+}$-binding proteins are already present in vivo. To average $[Ca^{2+}]_i$ over a longer period, the illumination could be weakened and prolonged. Alternatively, if the stimulus is repetitive, the flashes could be likewise repeated at a given phase delay in order to signal-average the response.

If not all the dye molecules are securely anchored when the flash arrives, the mobile molecules should not interfere so long as they do not bind after the flash. This is because they should get washed out of the tissue section during the histology. Also, if subcellular spatial resolution is not required, covalent reaction with cellular macromolecules should not be necessary, because the indicator molecules should remain trapped in their respective cells. Therefore R could be simply H or COO⁻. One would merely have to avoid membrane permeabilization during the subsequent processing.

Calibration of $[Ca^{2+}]_i$ would be easiest with detection of the ratio between the photolyzed and unphotolyzed species, since the absolute amount of indicator would not matter. Comparisons would be made with the appearance of protein gels or cells photolyzed while containing known $[Ca^{2+}]_i$ concentrations. The method should then tolerate a certain amount of crosstalk, for example incomplete spectra separation between the $Ca^{2+}$-free and $Ca^{2+}$-bound species, or insufficient light intensity or quantum yield to completely photolyze all the molecules that ought to photolyze, or imperfect antibody specificity. While these types of deficiencies would reduce the maximum possible image contrast between very high and very low $[Ca^{2+}]_i$, they would not invalidate the $[Ca^{2+}]_i$ reading so long as they also apply to the calibration protein gels or cells.

Figure 6:
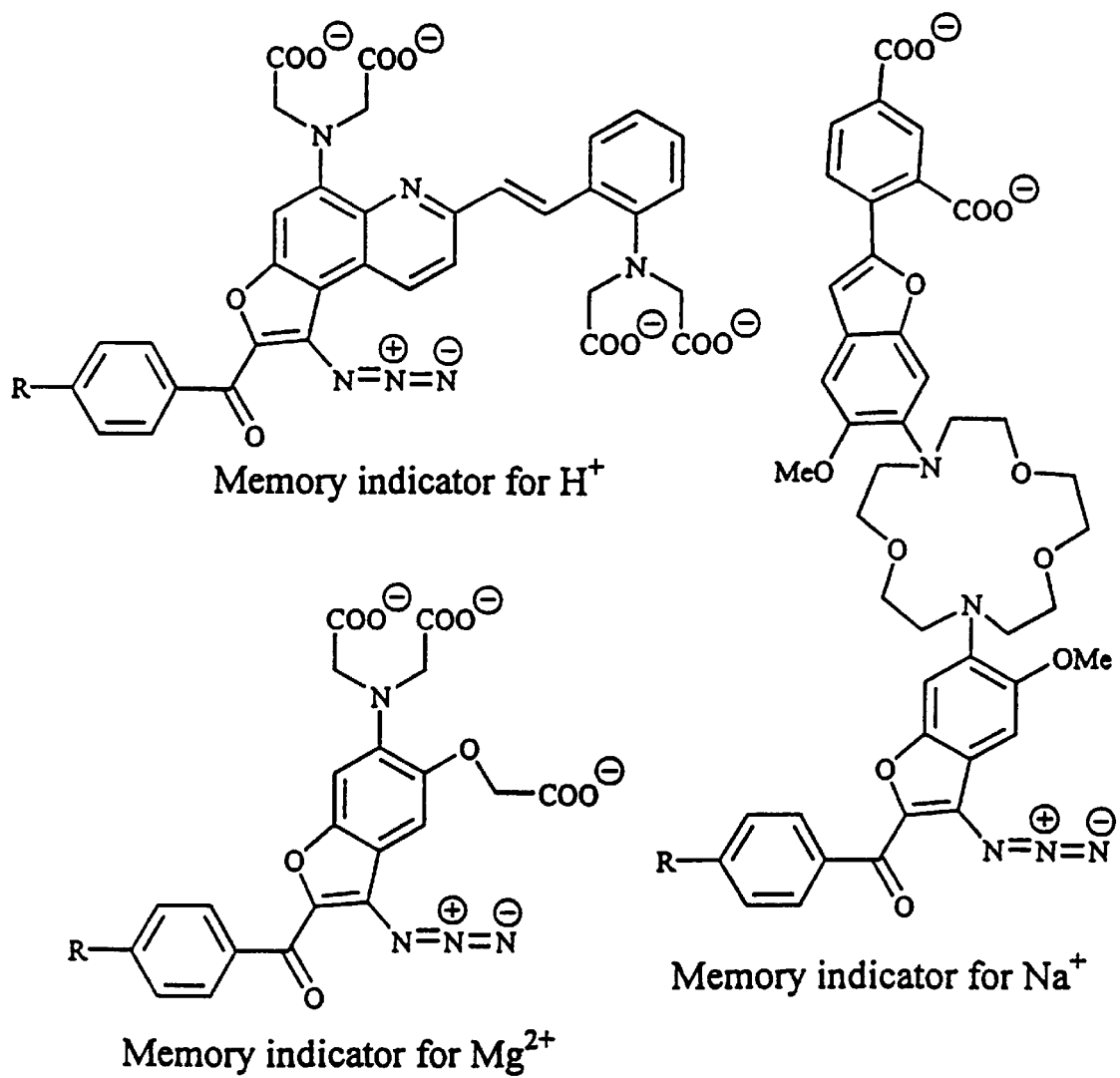
FIG. 6 shows memory indicators for other physiologically significant cations.

FIG. 6 shows how the memory indicator concept might be extended to other cations. The structure proposed as a memory indicator for $H^+$ is a hybrid of the present azidoketone with the known fluorescent pH indicator "quene-1" (Rogers, J., Hesketh, T. R., Smith, G. A., Metcalfe, J. C. (1983) *J Biol. Chem.* 258:5994–5997). Likewise the $Na^+$- and $Mg^{2+}$-memorizing molecules combine the azidoketone with known binding sites for those cations respectively (Minta, A., Tsien, R. Y. (1989) *J Biol. Chem.* 264:19449–19457; Raju, B., Murphy, E., Levy, L. A., Hall, R. D., London, R. E. (1989) *Am. J Physiol.* 256:C540–C548. Ligands which selectively bind to biologically significant analytes are known to those of skill in the art and it is contemplated that indicators made from all such ligands linked to chromophores with a photolabile group as described herein can be used in this invention.

The indicator would be loaded into the tissue by standard methods such as membrane-permeant, hydrolyzable esters, microinjection, or dialysis through a patch pipet. If subcellular resolution is desired, the indicator molecules should carry chemically reactive groups to covalently attach them to random cellular macromolecules. At the moment at which $[Ca^{2+}]_i$ is to be memorized, the specimen is illuminated with a brief flash of light of appropriate wavelengths. The local degree of progress of the photochemical reaction constitutes a latent but irreversible image of the $[Ca^{2+}]_i$ levels existing during the flash. Subsequent changes in $[Ca^{2+}]_i$ have no influence because the light necessary for the photochemistry is no longer being delivered. After stabilization of the tissue, for example by freezing or fixation and sectioning, and chemical removal of any remaining light-sensitive moieties, the latent image is visualized either by the difference in fluorescence of the molecules that have vs. have not undergone the photochemistry, or by standard techniques of immunocytochemistry with tagged antibodies specific for the same two sets of molecules.

EXAMPLE 1

SYNTHESIS OF MEM-1

Figure 8:
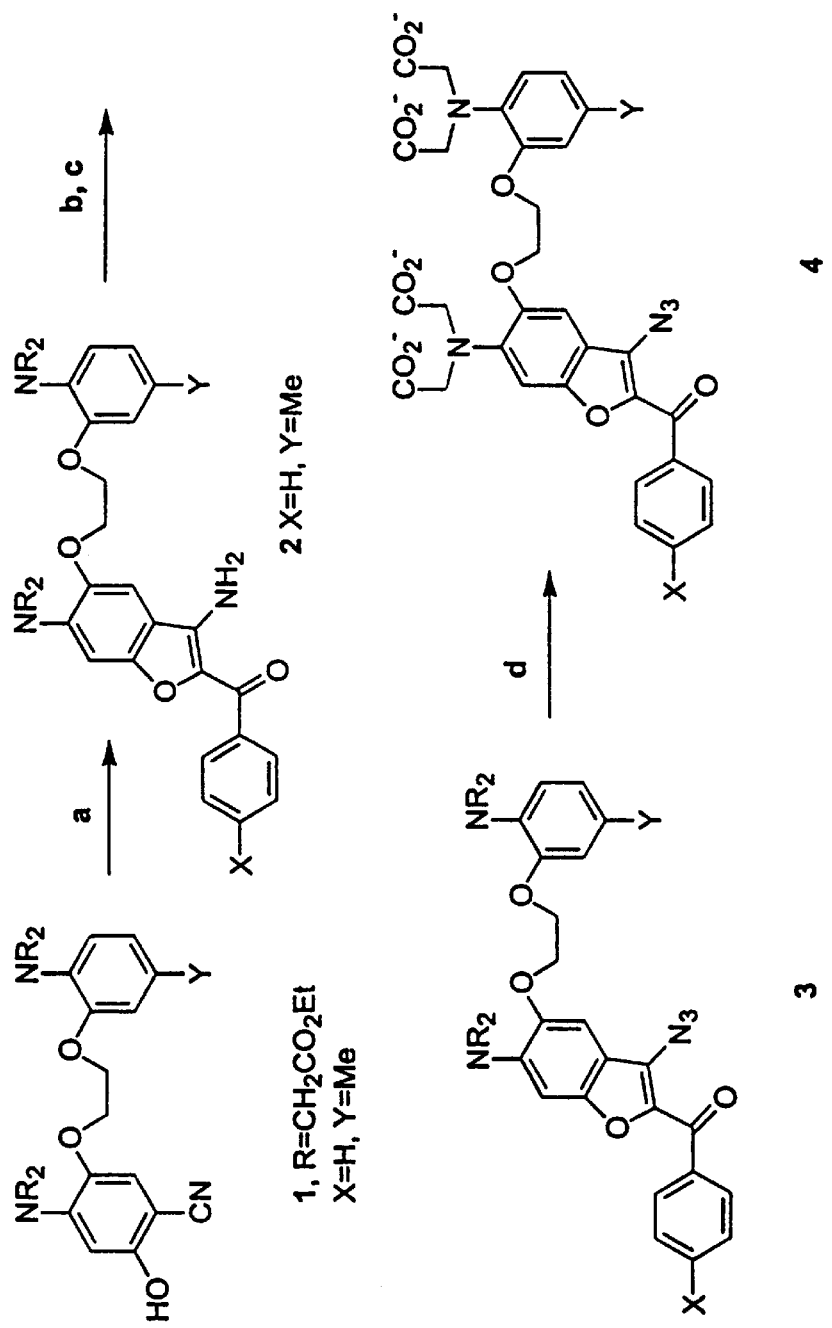
FIG. 8 shows a synthetic approach to memory indicators.

The synthesis of memory indicators is generally presented in FIG. 8. The synthetic scheme was carried out as follows:

Synthesis of the starting materials:

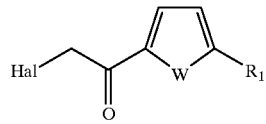

as described for Y=H, Z=O, Hal=Br (Pascal Y., *Ann. Chim.* 3:245–275, 1968) and Y=H, Z=S, NH, NMe (Arcoria, A., Fisichella, E. Maccarone, and Scarlata, G. *J. HeterocycL Chem.* 12:215–218, 1975).

Chemicals (Aldrich; Milwaukee, Wis., U.S.A.) and solvents (HPLC-grade, Fisher; Fair Lawn, N.J,, U.S.A.) were used directly as received unless otherwise noted. Chloroform and dimethylformamide (DMF) were dried over 4 Å molecular sieve.

Proton magnetic resonance spectra ($^1$H NMR) were recorded on a Gemini 200-MHz spectrometer (Varian; Palo Alto, Calif., U.S.A.) in $CDCl_3$ unless otherwise noted, and the chemical shifts are given in δ values relative to tetramethylsilane. Ultra-violet spectra were recorded on a Lambda Array 3840 spectrophotometer (Perkin-Elmer; Norwalk, CT, CA) or a Cary 3E UV-Visible spectrophotometer (Varian; Palo Alto, Calif., U.S.A.) at 20° C.

Thin layer chromatography (TLC) was carried out on precoated silica gel 60F-254 or reverse-phase RP-18, F-254 plates (E. Merck, EM Separations; Gibbstown, N.J., U.S.A.). For column chromatography, silica gel 60 (230–400 mesh, E. Merck) was used. All manipulations of compounds sensitive to near ultraviolet light were performed under an orange safety lamp.

Amine (2): Cyanophenol 1 (prepared as described in U.S. Pat. No. 5,552,555) (65 mg, 0.1 mmol), phenacyl bromide (0.12 mmol, 24 mg) and anhydrous $K_2CO_3$ in dry DMF (0.25 mL) were heated at 120° C. for 30 minutes. After cooling, $H_2O$ (5 mL) and HOAc (2 drops) were added and the crude product was extracted into ethyl acetate (3×10 mL). After drying ($Na_2SO_4$), evaporation and separation by silica gel chromatography (ethyl acetate:hexane 1:1) the product, 2 was obtained as yellow solid. Yield, 51 mg.

Azide (3): Amine 2 (30 mg, 0.039 mmol) was dissolved in HOAc (0.2 mL) at room temperature and added dropwise to an ice-cold solution of nitrosylhydrogen sulfate (NOHSO$_4$)(30 mg) in conc. H$_2$SO$_4$ (0.3 mL). After stirring on ice for 30 mins, the mixture was added dropwise to an ice-cold saturated a aqueous solution of NaN$_3$ (CARE: Hydrazoic acid formed; carry out in well-ventilated fumehood). The mixture was neutralized with sodium acetate trihydrate (2 g) and extracted with ethyl acetate (3×30 mL). After drying, the crude product was separated by silica gel chromatography (ethyl acetate:hexane 1:1) to give a yellow solid (17 mg after trituration with EtOH).

Preparation of Substituted Phenacyl Bromides

4-Trifluoroacetamido-acetophenone:
4-Aminoacetophenone (1 mmol, 135 mg) was dissolved in trifluoroacetic acid (1 mL) at −10° C. under argon. Trifluoroacetic anhydride (2 mmol, 0.28 mL) were added dropwise with stirring. The reaction mixture was allowed to warm to room temperature for 15 mins and then evaporated to dryness. The resulting solid was triturated with isopropyl ether to yield the product as a white solid (yield, 84%).

2'-Bromo-4-trifluoroacetamido-acetophenone:
4-Trifluoroacetamido-acetophenone (1.8 g, 8 mmol) were dissolved in dioxane:diethyl ether (1:1 v/v; 10 mL) and cooled to −15° C. Bromine (8.1 mmol, 0.42 mL) was added dropwise allowing the reaction mixture to decolorize between additions. After 20 minutes, the solution was poured into H$_2$O (50 mL) and extracted into ethyl acetate (3×30 mL), dried (Na$_2$SO$_4$) and evaporated. The crude product was recrystallized from 95% EtOH to yield the product as white crystals (Yield, 40%).

The intracellular calcium concentration can be memorized by ratio imaging and, for example, antibody staining.

The foregoing invention has been described in some detail by way of illustration and example, for purposes of clarity and understanding. Other embodiments are within the claims. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:
1. A compound comprising:
   a chromophore incorporating a photolabile group capable of undergoing an irreversible and detectable intramolecular chemical transformation upon irradiation by light, the chromophore being linked to a binding site capable of binding an analyte,
   the compound having a structure, represented by an azido-substituted aromatic ring A with additional substituents Y and Z and represented by the formula:

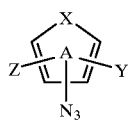

and the pharmaceutically acceptable salts and esters thereof wherein:
   wherein X is O and Y is a fused BAPTA or BAPTA-like derivative and is fused or attached to a single atom of A;
   Z is a substituent attached to A ortho to the azido group and is represented by R—C(O)—,
   wherein R is independently a hydrocarbyl radical or an heterocyclic aromatic radical,
   wherein the photolabile group comprises a β-azido, α,β-unsaturated carbonyl group and the chemical transformation is conversion of the β-azido, α,β-unsaturated carbonyl group to an isoxazole,
   wherein the analyte is a cation selected from the group consisting of Ca++, Na+, Mg++ and H+, and
   wherein binding of the analyte to the binding site alters an optical property of the chromophore, thus altering the ability of the photolabile group to undergo the chemical transformation upon irradiation.

2. The compound of claim 1, wherein the optical property is peak absorbance wavelength or quantum efficiency.

3. The compound of claim 1, wherein R is an aromatic radical.

4. The compound of claim 3, wherein the compound is selected from a group consisting of a compound represented by the formula:

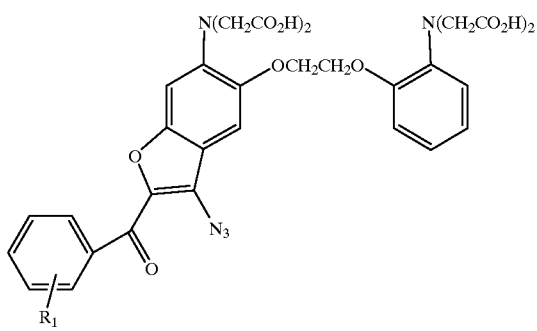

and the pharmaceutically acceptable salts and esters thereof, wherein R$_1$ is alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, di-lower-alkylcarbamoyl, carboxylic acid, ester, sulfonamide, phosphono, phosphoryl group, or arsono; and a compound represented by the formula:

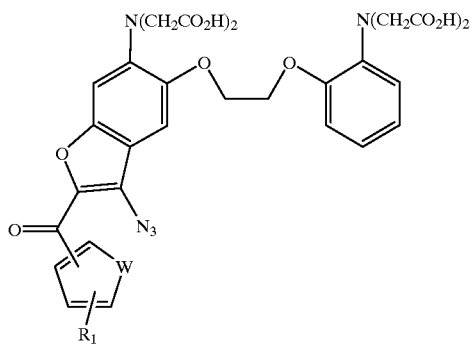

and the pharmaceutically acceptable salts and esters thereof, wherein $R_1$ is alkyl, lower-alkyl, cycloalkyl, hydroxylower-alkyl, aminolower-alkyl, hydroxyl, thiol, amino, halo, nitro, lower-alkylthio, lower-alkoxy, mono-lower-alkylamino, di-lower-alkylamino, acyl, hydroxycarbonyl, lower-alkoxycarbonyl, hydroxysulfonyl, lower-alkoxysulfonyl, lower-alkylsulfonyl, lower-alkylsulfinyl, trifluoromethyl, cyano, tetrazoyl, carbamoyl, lower-alkylcarbamoyl, di-lower-alkylcarbamoyl, carboxylic acid, ester, sulfonamide, phosphono, phosphoryl group, or arsono.

5. The compound of claim 4, wherein the lower-alkoxycarbonyl groups are esterfied to α-acyloxyalkylesters.

6. A method of memorizing an intracellular concentration of an analyte selected from the group consisting of Ca++, Na+, Mg++ and H+, the method comprising the steps of:

(a) loading a cell with an effective amount of a compound of claim 1 under conditions which do not alter the chromophore;

(b) irradiating the cell with a wavelength of light which selectively photolyzes compound which is not bound to the analyte, to form a chemically transformed product;

(c) detecting the presence of the transformed product and/or unphotolyzed compound; and (d) relating the presence of the transformed product and/or unphotolyzed compound to the intracellular concentration of the analyte.

7. The method of claim 6, further comprising converting unphotolyzed compound to a light insensitive product between the irradiating step and the detecting step.

8. The method of claim 7, wherein the detecting step comprises measuring an optical property of the chemically transformed product and/or unphotolyzed compound.

9. The method of claim 8, wherein the optical property is fluorescence.

10. The method of claim 9, wherein the fluorescence excitation and emission ratios of the chemically transformed product and/or unphotolyzed compound are measured.

11. The method of claim 7, wherein the converting step comprises reducing the unphotolyzed compound.

12. The method of claim 6, wherein the detecting step comprises:

(1) exposing the cell to an antibody against the chemically transformed product and/or unphotolyzed compound; and (2) detecting the binding of the antibody to the chemically transformed product and/or unphotolyzed compound.

13. The method of claim 12, wherein the antibody comprises a label.

14. A kit for memorizing analyte concentrations comprising a compound of claim 1, detection reagents and instructions for their use.

* * * * *